a substance effective for treating immunopathy where MCP-1 is involved is provided.

(12) United States Patent
Sugimura et al.

(10) Patent No.: US 7,342,106 B2
(45) Date of Patent: Mar. 11, 2008

(54) HUMAN ANTIHUMAN MCP-1 ANTIBODY AND ANTIBODY FRAGMENT THEREOF

(75) Inventors: Kazuhisa Sugimura, Kagoshima (JP); Toshihiro Nakashima, Kikuchi-gun (JP); Tsukasa Nishihara, Kikuchi-gun (JP)

(73) Assignee: Judicial Foundation The Chemo-Sero-Therapeutic Research Institute, Kumamato-Ken (JP)

( * ) Notice: Subject to any disclaimer, the term of this patent is extended or adjusted under 35 U.S.C. 154(b) by 132 days.

(21) Appl. No.: 10/527,823

(22) PCT Filed: Sep. 10, 2003

(86) PCT No.: PCT/JP03/11560

§ 371 (c)(1),
(2), (4) Date: Mar. 14, 2005

(87) PCT Pub. No.: WO2004/024921

PCT Pub. Date: Mar. 25, 2004

(65) Prior Publication Data

US 2006/0246069 A1    Nov. 2, 2006

(30) Foreign Application Priority Data

Sep. 12, 2002    (JP) ............... 2002-267184

(51) Int. Cl.
*C07H 21/02* (2006.01)
*C07K 16/00* (2006.01)
(52) U.S. Cl. .................. 536/23.1; 536/23.53
(58) Field of Classification Search ............ None
See application file for complete search history.

(56) References Cited

U.S. PATENT DOCUMENTS

2003/0162737 A1    8/2003    Egashira et al.

FOREIGN PATENT DOCUMENTS

| JP | 09-67399 A | 3/1997 |
|---|---|---|
| JP | 2000-297098 A | 10/2000 |
| WO | WO 01/89582 A1 | 11/2001 |
| WO | WO 02/02640 * | 1/2002 |
| WO | WO 02/02640 A2 | 1/2002 |

OTHER PUBLICATIONS

Lewin et al. Genes IV. Oxford University Press, p. 810, 1990.*
Li et al. Biochemistry 2000. 39:6296-6309.*
Rudikoff et al. Proc Natl Acad Sci USA 1982 vol. 79 pp. 1979-1983.*
Janeway et al. Immunobiology by Current Biology Ltd. 1990. Chapter 3, pp. 3:1-3:38.*
Akahoshi, et al, "Expression of monocytes chemotactic and activating factor in rheumatoid arthritis". Arthritis and Rheumatism. (Jun. 1993). 36(6):762-771.

Boring, et al, "Decreased lesion formation in CCR2 mice reveals a role for chemokinase in the initiation of atherosclerosis", Nature. (Aug. 27, 1998), 394:894-897.
Gong, et al, "An antagonist of monocytes chemoattractant protein 1 (MCP-1) inhibits arthritis in the MRL-*lpr* mouse model". J. Exp. Med. (Jul. 7, 1997). 186(1):131-137.
Gosling, et al, "MCP-1 deficiency reduces susceptibility to atherosclerosis in mice that overexpress human apolipoprotein B". Journal of Clinical Investigation. (Mar. 1999). 103(6):773-778.
Grob, et al, "Characterization of a receptor for human monocytes-derived neutrophil chemotactic factor interleukin-8". Journal of Biological Chemistry. (May 15, 1990). 265(14):8311-8316.
Kaji, et al, "Analysis of peptide motifs recognized with anti-MCP-1 monoclonal antibodies". Peptide Science. (2000) 33-66.
Kaji, et al, "Peptide mimics of monocytes chemoattractant protein-1 (MCP-1) with an antagonistic activity". J. Biochem. (2001). 129:577-583.
Koch, et al, "Enhanced production of monocytes chemoattractant protein-1 in rheumatoid arthritis". Journal of Clinical Investigation. (Sep. 1992). 90:772-229.
Kurihara, et al, "Defects in macrophage recruitment and host defense in mice lacking the CCR2 chemokine receptor". J. Exp. Med. (Nov. 17, 1997)., 186(10):1757-1762.
Lei, et al, "Characterization of the *Erwinia carotovora pelB* gene and its product pectate lyase". Journal of Bacteriology. (Sep. 1987). 169(9):4379-4383.
Marks, et al, "By-passing immunization: human antibodies from V-gene libraries displayed on phage". J. Mol. Biol. (1991). 222:581-597.
Ogata, et al, "The role of monocytes chemoattractant protein-1 (MCP-1) in the pathogenesis of collagen-induced arthritis in rats". Journal of Pathology. (1997). 182:106-114.
Schrier, et al, "Role of chemokines and cytokines in a reactivation model of arthritis in rats induced by injection with streptococcal cell walls". Journal of Leukocyte Biology. (Mar. 1998). 63:359-363.
Sylvester, et al, "Neutrophil attractant protein=1 and monocytes chemosttractant protein-1 in human serum". Journal of Immunology. (Sep. 15, 1993). 151(6):3292-3298.

(Continued)

*Primary Examiner*—Maher M. Haddad
*Assistant Examiner*—Chun Crowder
(74) *Attorney, Agent, or Firm*—Browdy and Neimark, PLLC

(57) ABSTRACT

A substance effective for treating immunopathy where MCP-1 is involved is provided. scFv having a high affinity to human MCP-1 was obtained using phage antibody technique. Based on information of VH chain and VL chain obtained from said scFv, a human anti-human MCP-1 antibody and a human anti-human MCP-1 antibody fragment are obtained. Said antibody and antibody fragment are expected to be useful as a medicament for treating inflammation and immunopathy caused by MCP-1.

10 Claims, 5 Drawing Sheets

OTHER PUBLICATIONS

Wada, et al, "Intervention of crescentic glomerulonephritis by antibodies to monocytes chemotactic and activating factor (MCAF/MCP-1)". FASEB J. (1996). 10:1418-1425.

Yoshimura, et al, "Human monocytes chemoattractant protein-1 (MCP-1): Full-length cDNA cloning, expression in mitogen-stimulated blood mononuclear leukocytes, and sequence similarity to mouse competence gene JE", FEB Letters. (Feb. 1989). 244(2):487-493.

Yoshimura, et al, "production and characterization of mouse monoclonal antibodies against human monocytes chemoattractant protein=1". Journal of Immunology. (Oct. 1, 1991). 147(7):2229-2233.

Youssef, et al, "C-C chemokine-encoding DNA vaccines enhance breakdown of tolerance to their gene products and treat ongoing adjuvant arthritis". Journal of Clinical Investigation. (Aug. 2000). 106(3):361-371.

* cited by examiner

```
                        SEQUENCE LISTING

<160> NUMBER OF SEQ ID NOS: 14

<210> SEQ ID NO 1
<211> LENGTH: 366
<212> TYPE: DNA
<213> ORGANISM: Homo sapiens

<400> SEQUENCE: 1 cag gta cag ctg cag cag tca ggg gct gag gtg aag aag cct ggg tcc        48
Gln Val Gln Leu Gln Gln Ser Gly Ala Glu Val Lys Lys Pro Gly Ser
1               5                   10                  15 tcg gtg aag gtc tcc tgc aag gct tct gga ggc acc ttc agc agc tat        96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
        35                  40                  45 gga ggt ttt gat cct gaa gat ggt gaa aca atc tac gca cag aag ttc       192
Gly Gly Phe Asp Pro Glu Asp Gly Glu Thr Ile Tyr Ala Gln Lys Phe
    50                  55                  60 cag ggc aga gtc acc atg acc gag gac aca tct aca gac aca gcc tac       240
Gln Gly Arg Val Thr Met Thr Glu Asp Thr Ser Thr Asp Thr Ala Tyr
65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                85                  90                  95 gca aca gat ctt ggc gga ggt gac tac tac ggt atg gac gtc tgg           336
Ala Thr Asp Leu Gly Gly Gly Asp Tyr Tyr Tyr Gly Met Asp Val Trp
            100                 105                 110 ggc cca ggg acc acg gtc acc gta tcc tca                               366
Gly Pro Gly Thr Thr Val Thr Val Ser Ser
        115                 120

<210> SEQ ID NO 2
<211> LENGTH: 122
<212> TYPE: PRT
<213> ORGANISM: Homo sapiens

<400> SEQUENCE: 2

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Leu Gly Gly Gly Asp Tyr Tyr Tyr Gly Met Asp Val Trp
            100                 105                 110
Gly Pro Gly Thr Thr Val Thr Val Ser Ser
        115                 120
```

<210> SEQ ID NO 3
<211> LENGTH: 5
<212> TYPE: PRT
<213> ORGANISM: Homo sapiens
<220> FEATURE:
<223> OTHER INFORMATION: CDR1 corresponding to amino acids No. 31 to No.
      35 in SEQ ID NO: 2

<400> SEQUENCE: 3

```
Ser Tyr Ala Ile Ser
1               5
```

<210> SEQ ID NO 4
<211> LENGTH: 17
<212> TYPE: PRT
<213> ORGANISM: Homo sapiens
<220> FEATURE:
<223> OTHER INFORMATION: CDR2 corresponding to amino acids No. 50 to No.
      66 in SEQ ID NO: 2

<400> SEQUENCE: 4

```
Gly Phe Asp Pro Glu Asp Gly Glu Thr Ile Tyr Ala Gln Lys Phe Gln
1               5                   10                  15
Gly
```

<210> SEQ ID NO 5
<211> LENGTH: 13
<212> TYPE: PRT
<213> ORGANISM: Homo sapiens
<220> FEATURE:
<223> OTHER INFORMATION: CDR3 corresponding to amino acids No. 99 to No.
      111 in SEQ ID NO: 2

<400> SEQUENCE: 5

```
Asp Leu Gly Gly Gly Asp Tyr Tyr Tyr Gly Met Asp Val
1               5                   10
```

<210> SEQ ID NO 6
<211> LENGTH: 324
<212> TYPE: DNA
<213> ORGANISM: Homo sapiens

<400> SEQUENCE: 6

```
gac atc cag ttg acc cag tct cct tcc acc ctg tct gct tct gtc ggg       48
Asp Ile Gln Leu Thr Gln Ser Pro Ser Thr Leu Ser Ala Ser Val Gly
1               5                   10                  15 gac aga gcc acc atc tct tgc cgg tct agt cag agc att aac acc tat       96
Asp Arg Ala Thr Ile Ser Cys Arg Ser Ser Gln Ser Ile Asn Thr Tyr
                20                  25                  30 tta cat tgg tat cag cag aaa cca ggg gaa gcc cct aaa ctc ctg atc       144
Leu His Trp Tyr Gln Gln Lys Pro Gly Glu Ala Pro Lys Leu Leu Ile
            35                  40                  45
```

-continued

```
tat gct gct tcc acc ttg caa agt ggg gtc cca tca aga ttc agt ggc      192
Tyr Ala Ala Ser Thr Leu Gln Ser Gly Val Pro Ser Arg Phe Ser Gly
    50                  55                  60 agt gga tct ggg aca gat ttc act ctc acc atc acc act ctc caa cct      240
Ser Gly Ser Gly Thr Asp Phe Thr Leu Thr Ile Thr Thr Leu Gln Pro
65                  70                  75                  80 gaa gat ttt gca act tat tac tgc caa cag agt ttc act acc cca ctc      288
Glu Asp Phe Ala Thr Tyr Tyr Cys Gln Gln Ser Phe Thr Thr Pro Leu
                85                  90                  95 act ttc ggc gga ggg acc aag gtg gag atc aaa cgt                      324
Thr Phe Gly Gly Gly Thr Lys Val Glu Ile Lys Arg
            100                 105
```

<210> SEQ ID NO 7
<211> LENGTH: 108
<212> TYPE: PRT
<213> ORGANISM: Homo sapiens

<400> SEQUENCE: 7

Asp Ile Gln Leu Thr Gln Ser Pro Ser Thr Leu Ser Ala Ser Val Gly
1               5                   10                  15

Asp Arg Ala Thr Ile Ser Cys Arg Ser Ser Gln Ser Ile Asn Thr Tyr
            20                  25                  30

Leu His Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Thr Thr Leu Gln Pro
65                  70                  75                  80

Glu Asp Phe Ala Thr Tyr Tyr Cys Gln Gln Ser Phe Thr Thr Pro Leu
                85                  90                  95

Thr Phe Gly Gly Gly Thr Lys Val Glu Ile Lys Arg
            100                 105

<210> SEQ ID NO 8
<211> LENGTH: 11
<212> TYPE: PRT
<213> ORGANISM: Homo sapiens
<220> FEATURE:
<223> OTHER INFORMATION: CDR1 corresponding to amino acids No. 24 to No.
      34 in SEQ ID NO: 7

<400> SEQUENCE: 8

Arg Ser Ser Gln Ser Ile Asn Thr Tyr Leu His
1               5                   10

<210> SEQ ID NO 9
<211> LENGTH: 7
<212> TYPE: PRT
<213> ORGANISM: Homo sapiens
<220> FEATURE:
<223> OTHER INFORMATION: CDR2 corresponding to amino acids No. 50 to No.
      56 in SEQ ID NO: 7

<400> SEQUENCE: 9

Ala Ala Ser Thr Leu Gln Ser
1               5

<210> SEQ ID NO 10
<211> LENGTH: 9
<212> TYPE: PRT
<213> ORGANISM: Homo sapiens
<220> FEATURE:

```
<223> OTHER INFORMATION: CDR3 corresponding to amino acids No. 89 to No.
      97 in SEQ ID NO: 7

<400> SEQUENCE: 10

Gln Gln Ser Phe Thr Thr Pro Leu Thr
1               5

<210> SEQ ID NO 11
<211> LENGTH: 42
<212> TYPE: DNA
<213> ORGANISM: Artificial
<220> FEATURE:
<223> OTHER INFORMATION: VH chain sense primer

<400> SEQUENCE: 11
cgtggctcct gggcccacag ccaggtacag ctgcagcagt ca                          42

<210> SEQ ID NO 12
<211> LENGTH: 20
<212> TYPE: DNA
<213> ORGANISM: Artificial
<220> FEATURE:
<223> OTHER INFORMATION: VH chain antisense primer

<400> SEQUENCE: 12
tgaggatacg gtgaccgtgg                                                   20

<210> SEQ ID NO 13
<211> LENGTH: 42
<212> TYPE: DNA
<213> ORGANISM: Artificial
<220> FEATURE:
<223> OTHER INFORMATION: VL chain sense primer

<400> SEQUENCE: 13
cgtggctcct gggcccacag cgacatccag ttgacccagt ct                          42

<210> SEQ ID NO 14
<211> LENGTH: 20
<212> TYPE: DNA
<213> ORGANISM: Artificial
<220> FEATURE:
<223> OTHER INFORMATION: VL chain antisense primer

<400> SEQUENCE: 14
acgtttgatc tccaccttgg                                                   20
```

HUMAN ANTIHUMAN MCP-1 ANTIBODY AND ANTIBODY FRAGMENT THEREOF

TECHNICAL FIELD

The present invention relates to a human anti-human Monocyte chemoattractant protein-1 (hereinafter referred to as "human MCP-1") antibody that binds to human MCP-1 to thereby block the biological activity thereof or a fragment of said antibody. The antibody and a fragment of said antibody are expected to be useful as a medicament for treating inflammation and immunopathy caused by MCP-1.

BACKGROUND ART

Chemokines are a peptide of 8 to 10 kDa that plays an important role in migration and activation of leukocytes. Chemokines are classified into four subgroups, i.e. "C chemokines", "CC chemokines", "CXC chemokines" and "CX3C chemokines", based on positions of the first two cysteines (C) among the four cysteines present at the N-terminus of chemokines. MCP-1, one of chemokines belonging to CC chemokines subfamily, is a monocyte chemotactic-activating factor with 76 amino acid residues that was cloned from human glioma cell line and monocytic leukemia cell line in 1989 (see e.g. Yoshimura, T. et al., "FEBS Letter", 1989, Vol. 244, p. 487-493). MCP-1 is a multifunctional molecule that is produced by monocytes, vascular endothelial cells, and fibroblasts and acts on monocytes, T cells and basophiles to enhance their migrating activity, production and release of active oxygen and lysosome enzyme, production and induction of cytokines, degranulation of basophiles, induction of adhesive molecules expression, production and release of histamine and leukotrienes, etc.

With progress of analysis using disease model animals, especially for chronic inflammation, MCP-1 has been indicated to be responsible for some inflammatory diseases (see e.g. Schrier, D. J. et al., "Journal of Leukocyte Biology", 1998, Vol. 63, p. 359-363). Besides, it has been reported that inhibition of MCP-1 activity in these disease model animals resulted in reduction of symptoms. For instance, it has been reported that administration of anti-MCP-1 antibody to collagen-induced arthritis (hereinafter also referred to as "CIA") model or adjuvant-induced arthritis model of rats provides preventive and treating effects for arthritis to alleviate arthritic symptoms (see e.g. Youssef, S. et al., "Journal of Clinical Investigation", 2000, Vol. 106, p. 361-371; and Ogata, H. et al., "Journal of Pathology", 1997, Vol. 182, p. 106-114). It has also been reported that, in case of MRL-lpr mice where arthritis spontaneously occurs and lasts throughout the life, arthritis aggravates when MCP-1 is administered but is reduced when antagonist to MCP-1 is administered (see e.g. Gong, J. H. et al., "Journal of Experimental Medicine", 1997, Vol. 186, p. 131-137).

Moreover, with progress of analysis using mice with deficiency in genes of MCP-1 and its receptor CCR2, it has been indicated that in some inflammatory diseases MCP-1/CCR2 is essential for macrophage invasion involved in onset of disease. For instance, it has been reported that MCP-1 deficiency in autoimmune mice inhibited migration of macrophages and T cells to protect the kidney, the lung and skin, resulting in prolonging of life, and that macrophage invasion to inflammation experimentally induced in the abdomen was inhibited in knockout mice with disrupted CCR2 gene (see e.g. Kurihara, T. et al., "Journal of Experimental Medicine", 1997, Vol. 186, p. 1757-1762). There is also a report that deficiency in MCP-1 or CCR2 in arteriosclerosis model mice inhibited macrophage migration on the artery wall and formation of sclerotic focus (see e.g. Gosling, J. et al., "Journal of Clinical Investigation", 1999, Vol. 103, p. 773-778; and Boring L. et al., "Nature", 1998, Vol. 394, p. 894-897).

In relation to human diseases, higher MCP-1 level in synovial fluid in rheumatoid arthritis (hereinafter also referred to as "RA") patients was found as compared to that of osteoarthritis patients, implying that MCP-1 may play a major role in induction/enhancement of inflammatory cell invasion and inflammation (see e.g. Akahoshi, T. et al. "Arthritis and Rheumatism", 1993, Vol. 36, p. 762-771; and Koch, A E. et al., "Journal of Clinical Investigation", 1992, Vol. 90, p. 772-779). Epidemiological investigation also revealed that MCP-1 may be involved in onset of myocardial infarction and arteriosclerosis and an activity to inhibit the cell migration mediated by MCP-1 can be a risk factor of these diseases. It is thus expected that an anti-MCP-1 antibody may be used for inhibiting a cell migration mediated by MCP-1 to thereby prevent and treat myocardial infarction and arteriosclerosis.

As described above, it has been revealed that MCP-1 is involved in invasion of inflammatory cells and induction of inflammation in chronic inflammatory diseases and arteriosclerosis. It is thus expected that development of a specific monoclonal antibody that neutralizes the biological activity of MCP-1 would provide a clinical means for effectively treating diseases where macrophage invasion is a main factor. Several monoclonal antibodies binding to MCP-1 have already been obtained from mice and rats and were reported to inhibit macrophage invasion in rat Masugi type nephritis and to inhibit macrophage invasion, increase in right ventricular pressure and hypertrophy of the inner membrane of pulmonary arteriole in rat pulmonary hypertension model (see e.g. Wada, T. et al., "FASEB Journal", 1996, Vol. 10, p. 1418-1425; and Kimura, H. et al., "Lab. Invest.", 1998, Vol. 78, p. 571-581).

DISCLOSURE OF THE INVENTION

Technical Problems to be Solved by the Invention

However, since the anti-MCP-1 monoclonal antibodies as described above are derived from heterologous animals, they would be recognized and removed as a foreign substance when administered to human and hence would not be suited for use as a medicament. This is in particular the case in the treatment of chronic autoimmune diseases such as RA where continual administration of drugs is required for a long period of time and hence occurrence of antibodies to the administered antibody becomes a problem. As a means to obviate this problem, a method for obtaining an anti-human MCP-1 monoclonal antibody derived from human is known (see e.g. Japanese patent publication No. 67399/1997). Namely, human lymphocytes producing an anti-human MCP-1 antibody were transformed with Epstein-Barr virus (hereinafter also referred to as "EBV") and the resulting transformant cells were cell-fused with myeloma cells to produce hybridomas from which a human anti-human MCP-1 monoclonal antibody has been obtained. However, the antibody obtained in said publication is an IgM class antibody and thus is not likely to provide high affinity and can less easily be handled as compared to an IgG class antibody. Besides, from practical point of view, there is also a problem that EBV transformant cells could produce antibodies only at a low level. In addition, according to the disclosure of Japanese patent publication No. 67399/1997, said IgM antibody against human MCP-1 is confirmed to have a binding activity to human MCP-1 but not a neutralizing activity.

As an alternative to the methods described above, it might also be possible to humanize a mouse monoclonal antibody against human MCP-1 using the genetic engineering technique. However, even with a humanized antibody, a possibility could not be denied that an antibody (inhibition antibody) inhibiting the activity of an anti-human MCP-1 antibody is produced in chronic disease patients who receive repetitive or prolonged administration of drugs.

Means to Solve the Problems

Under the circumstances, the present inventors, as a result of diligent investigation, have obtained a single chain Fv (scFv) molecule of fully human anti-human MCP-1 antibody from a phage display library constructed from immunoglobulin VH chain and VL chain genes prepared from peripheral blood B lymphocytes from healthy adults, and elucidated VH and VL chains of said antibody. The fully human anti-human MCP-1 antibody prepared by using the sequence information of said human antibody and a fragment of said antibody may bind to human MCP-1 and inhibit the biological activity thereof and hence are provided for the prevention/treatment of inflammatory diseases.

More Efficacious Effects than Prior Art

As described above, scFv against human MCP-1 derived from human according to the present invention is shown to specifically bind to human MCP-1 to thereby inhibit the cell migration mediated by human MCP-1. It is thus expected that said scFv as well as a human anti-human MCP-1 antibody in which VH chain and VL chain of said scFv are combined with a human antibody constant region or a portion thereof or a fragment of said human anti-human MCP-1 antibody are applied to the treatment of diseases wherein human MCP-1 is involved, including e.g. chronic inflammatory diseases and arteriosclerosis. With these antibodies, including those which bound to human MCP-1 but did not exhibit an inhibitory activity to human MCP-1, it is also possible to measure blood level of human MCP-1 to thereby monitor the progress of the diseased conditions.

BEST MODE FOR CARRYING OUT THE INVENTION

Figure 1:
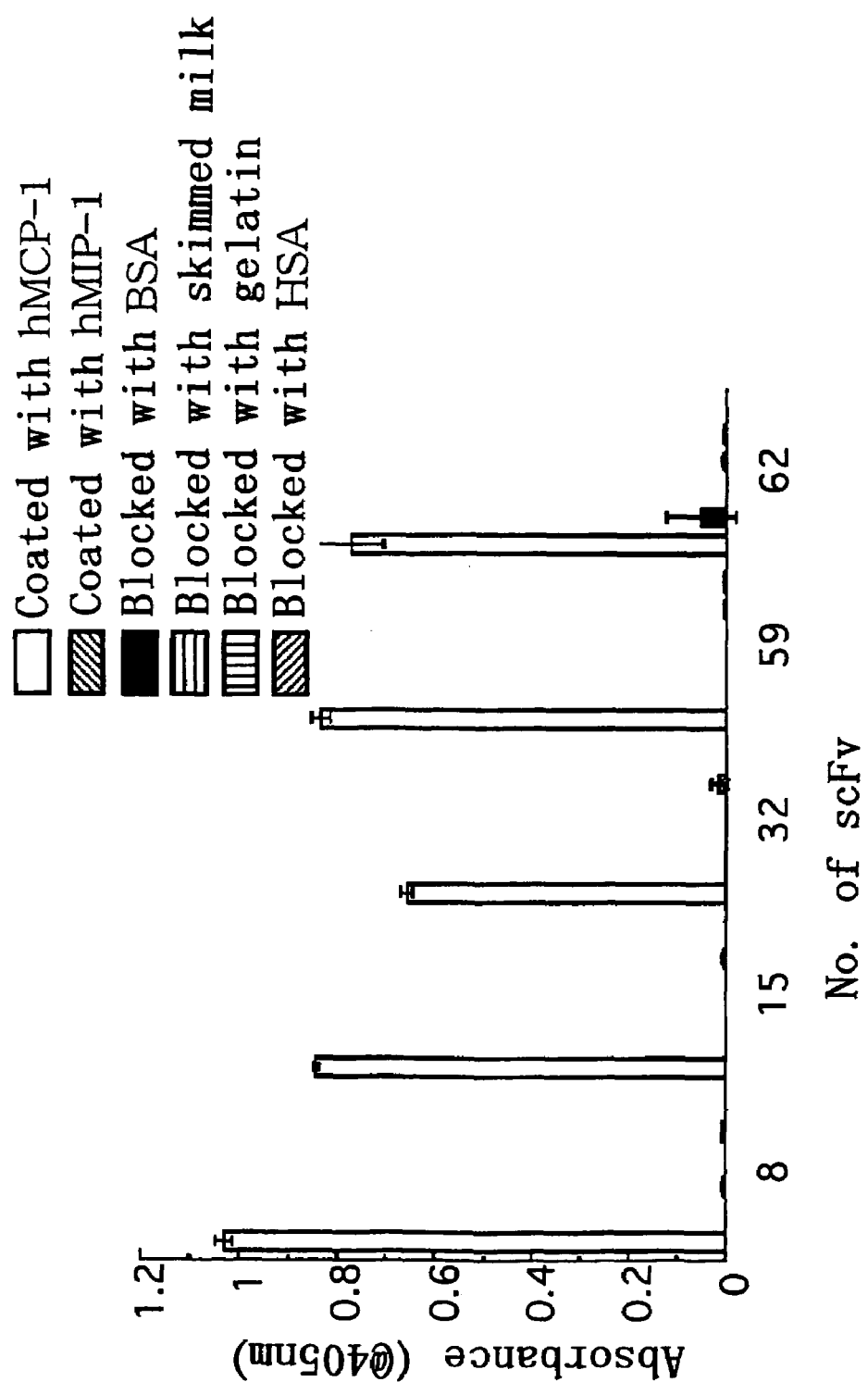
FIG. 1 is a graph showing the results of ELISA where specificity of scFv of isolated clones with human MCP-1 is assessed.

The human antibody and a fragment of said antibody of the present invention may be prepared e.g. by the procedures as described hereinbelow.

mRNAs were extracted from peripheral blood B lymphocytes from healthy adults and immunoglobulin VH chain and VL chain genes were amplified by RT-PCR with primer pairs defining both ends of the VH chain and VL chain genes to provide each population of H chain and L chain V region genes with diverse sequences. Then, amplification was further performed with a DNA encoding a peptide linker and with primer pairs defining both ends of said DNA so that the ends of said DNA are linked to the H chain gene and L chain gene, respectively, to prepare a population of scFv DNAs with random combination of H chain and L chain V region genes. The obtained scFv DNAs were incorporated into phagemid vector pCANTAB5E to prepare an scFv display phage library. The library is then reacted with human MCP-1 immobilized on a plastic tube. After scFv phages not reacted were removed by washing, scFv phage clones bound to human MCP-1 were eluted with an acid. scFv DNAs are prepared from the isolated phage clones and incorporated into an expression vector and host cells transformed with said expression vector are cultured by the conventional manner to provide the desired scFv protein alone.

For expression of scFv DNAs, the expression may be performed in *E. coli*. For expression in *E. coli*, a signal sequence for secretion of an antibody may functionally be linked to scFv to be expressed with such a useful promoter as routinely used in the art. Such a promoter includes, for instance, lacZ promoter, araB promoter, etc. For a signal sequence for secretion of scFv, pelB signal sequence may be used (Lei, SP. et al., J. Bacteriol., 1987, 169: 4379-4383) for expression in periplasm of *E. coli*. For expression in culture supernatant, a signal sequence of g3 protein of M13 phage may also be used.

The scFv thus expressed may be isolated from within and without the cells and purified to uniformity. Since the scFv expressed in accordance with the present invention has an E tag sequence at its C-terminal, it can easily be purified with affinity chromatography using an anti-E tag antibody in a short period of time. It can also be purified by a combination of the conventional isolation/purification processes used in the protein chemistry. For instance, the antibody may be isolated and purified by a combination of ultrafiltration, salting-out method, and column chromatography such as gel filtration, ion exchange, or hydrophobic chromatography.

The scFv protein obtained in accordance with the present invention was found to have a biding activity to human MCP-1. As a measurement of an antigen-biding activity of the anti-human MCP-1 antibody as used in the present invention, ELISA, BIAcore, etc. may be used. For instance, in case of ELISA, a sample containing the desired anti-human MCP-1 antibody or a fragment of said antibody, such as culture supernatant of *E. coli* or a purified antibody, may be added to a 96-well plate to which human MCP-1 is immobilized. To the plate may then be added a secondary antibody labeled with an enzyme such as peroxidase. The plate may be incubated, washed, and added with a chromogenic substrate TMBZ and absorbance is determined to thereby assess an antigen-binding activity.

Moreover, the scFv protein obtained in accordance with the present invention was found to inhibit the cell migration mediated by human MCP-1. Migration (Chemotaxis) of sensitive cells by human MCP-1 may be investigated with chemotaxis assay routinely used in the art, e.g. as described by Grob et al. (Grob P M. et al., J. Biol. Chem., 1990, 265: 8311-8316). Specifically, using a commercially available chemotaxis chamber, each of the anti-human MCP-1 antibody and human MCP-1 are diluted with a culture solution such as RPMI1640 and mixed together, and the mixture is incubated at room temperature for a fixed time and then added to the lower part of the chamber partitioned with a filter. Then, a suspension of human MCP-1 sensitive cells such as, for instance, monocytic cell line THP-1, or human peripheral blood mononuclear cells (hereinafter also referred to as "PBMC") is added to the upper part of the chamber and left to stand at 37° C. for a fixed time. Migrating cells will move towards the lower part of the chamber through the filter attached thereto. Thus, cells adhered to the filter may be dyed with e.g. Giemsa staining for counting a cell number. Alternatively, a cell number may be counted for cells moved to the lower part of the chamber with e.g. a Coulter counter. In place of the chamber described above, commercially available disposable assay cells for chemotaxis assay may also be used. The chemotaxis assay system revealed that the scFv protein of the present invention inhibited the cell migration mediated by human MCP-1.

As described above, since the scFv protein obtained in accordance with the present invention may inhibit the cell migration mediated by human MCP-1 in a concentration dependent manner, it is expected to be efficacious for the prevention or treatment of diseases induced by said cell migration.

The amino acid sequences of VH and VL chains of the above scFv clone having the inhibitory activity as well as the nucleotide sequences coding therefor are indicated in SEQ ID NOs: 1 and 2 (VH chain) and in SEQ ID NOs: 6 and 7 (VL chain), respectively.

In addition, the amino acid sequences of complementarity determining regions (CDR1 to CDR3), which are included in the above amino acid sequences, of VH and VL chains are shown below.

[VH Chain]

```
CDR1:  Ser Tyr Ala Ile Ser              (SEQ ID NO: 3)

CDR2:  Gly Phe Asp Pro Glu Asp Gly      (SEQ ID NO: 4)
       Glu Thr Ile Tyr Ala Gln Lys
       Phe Gln Gly

CDR3:  Asp Leu Gly Gly Gly Asp Tyr      (SEQ ID NO: 5)
       Tyr Tyr Gly Met Asp Val
```

[VL Chain]

```
CDR1:  Arg Ser Ser Gln Ser Ile Asn      (SEQ ID NO: 8)
       Thr Tyr Leu His

CDR2:  Ala Ala Ser Thr Leu Gln Ser      (SEQ ID NO: 9)

CDR3:  Gln Gln Ser Phe Thr Thr Pro      (SEQ ID NO: 10)
       Leu Thr
```

The VH and VL chains of the present invention include those having the amino acid sequences as described above wherein one or several amino acid residues are deleted, substituted or added.

Although the VH chain and/or the VL chain of the human anti-human MCP-1 antibody as disclosed herein were obtained in the form of scFv by using the phage antibody technique, the present invention encompasses a human anti-human MCP-1 antibody in the immunoglobulin form wherein the disclosed VH chain and/or VL chain are combined with a constant region of a human immunoglobulin, a human anti-human MCP-1 antibody fragment such as Fab, Fab' or F(ab')$_2$ wherein the disclosed VH chain and/or VL chain are combined with a portion of a constant region of a human immunoglobulin, and other human anti-human MCP-1 antibody fragment such as a human anti-human MCP-1 single chain antibody (scAb) wherein scFv is combined with a constant region of a human immunoglobulin, as well as gene fragments encoding these antibodies and the antibody fragments. The present invention further encompasses a modified protein molecule wherein a high molecular weight modifying agent such as polyethylene glycol is combined with these antibody and antibody fragment protein molecules. For preparing scFv in which each Fv of the H chain and the L chain are linked together with a suitable linker, a peptide linker to be used may be any single chain peptide having e.g. 10-25 amino acid residues.

INDUSTRIAL APPLICABILITY

As described above, the human anti-human MCP-1 antibody and the fragment molecules of said antibody according to the present invention, containing a variable region of a human anti-human MCP-1 antibody, may potentially interact with human MCP-1 to thereby inhibit the binding between human MCP-1 and a human MCP-1 receptor. In addition, the human anti-human MCP-1 antibody and the fragment molecules of said antibody according to the present invention may inhibit various immune responses induced by human MCP-1 and hence may be used as a medicament for the prevention and treatment of inflammation and immunopathy induced by said immune responses, e.g. as an anti-inflammatory agent or a medicament for the treatment and prevention of autoimmune diseases. Besides, the antibody and a fragment thereof of the present invention is expected to contribute to the prevention and treatment of myocardial infarction and arteriosclerosis.

The present invention is explained in more detail by means of the following Examples but should not be construed to be limited thereto.

EXAMPLE 1

Construction of Phage Library from Healthy Donors

Phage library was constructed as reported by J. D. Marks et al., J. Mol. Biol., 222: 581-597, 1991 with some modification, using lymphocytes from peripheral blood taken from 20 healthy donors as a starting material.

Namely, lymphocytes were isolated from peripheral blood taken from 20 healthy donors by sedimentary centrifugation with Ficol, washed thoroughly with PBS and then treated with ISOGEN (NIPPON GENE CO., LTD) to prepare a total RNA. The obtained total RNA was divided into four samples and from each of the samples were prepared cDNAs with primers specific to constant regions of either human IgG, IgM, κ chain or λ chain using first strand cDNA synthesis kit (Pharmacia biotech). Using each of the obtained cDNAs as a template, each of antibody V region genes were amplified by polymerase chain reaction (PCR) using primers specific to either of combinations of VH(γ or μ) and JH, Vκ and Jκ, or Vλ and Jλ, as described by Marks et al.

Then, VH(γ or μ) and Vκ, and VH(γ or μ) and Vλ, were linked together with a linker DNA by assembly PCR (Mc-Cafferty, J. et al.: Antibody Engineering—A Practical Approach, IRL Press, Oxford, 1996) to prepare single chain scFv DNAs. The obtained scFv DNAs were added with NotI and SfiI restriction sites using PCR, electrophoresed on agarose gel and then purified. The purified scFv DNAs were digested with the restriction enzymes NotI (Takara) and SfiI (Takara) and then cloned into phagemid pCANTAB5E (Pharmacia). The obtained phagemids pCANTAB5E where scFv DNA was bound were introduced into E. coli TG1 cells by electroporation for each of VH(γ)-Vκ, VH(γ)-Vλ, VH(μ)-Vκ, and VH(μ)-Vλ. From the number of the transformed TG1 cells, it was assessed that VH(γ)-Vκ, VH(γ)-Vλ, VH(μ)-Vκ and VH(μ)-Vλ exhibited diversity of $1.1 \times 10^8$, $2.1 \times 10^8$, $8.4 \times 10^7$ and $5.3 \times 10^7$ clones, respectively. With M13KO7 helper phage, phage antibodies were expressed on the transformed TG1 cells to prepare scFv display phage library derived from healthy donors.

EXAMPLE 2

Panning

Human MCP-1 was dissolved in 1 mL 0.1M $NaHCO_3$ and the solution was incubated in 35 mm dish (Iwaki) at 4° C. overnight to immobilize IL-6. To the dish was added 0.5% gelatin/PBS for blocking at 20° C. for 2 hours and then the dish was washed six times with 0.1% Tween20-PBS. To the dish was then added 0.9 mL of the single chain antibody display phage solution ($1 \times 10^{12}$ tu/mL of the antibody phage library derived from healthy donors) for reaction.

After washing the dish ten times with 0.1% Tween20-PBS, 11.0 mL glycine buffer (pH 2.2) was added to elute single chain antibody display phages bound to human MCP-1. After adjusting pH by adding 1M Tris (hydroxymethyl)-aminomethane-HCl, pH9.1, the eluted phages were infected to E. coli TG1 cells at logarithmic growth phase. The infected TG1 cells were centrifuged at 3,000×g for 10 minutes. Supernatant was removed, suspended in 200 μL 2×YT culture medium, plated on SOBAG plate (SOB plate containing 2% glucose, 100 μg/ml ampicillin) and then incubated overnight in an incubator at 30° C. The resulting colonies were suspended and recovered in a suitable amount of 2×YT culture medium with a scraper (Coastor).

The obtained TG1 solution (50 μL) was inoculated on 30 mL 2×YT culture medium and rescued with a helper phage to prepare a phage library after screening. For each of the phage libraries VH(γ)-Vκ, VH(γ)-Vλ, VH(μ)-Vκ and VH(μ)-Vλ derived from healthy donors, four pannings in total were performed with the human MCP-1 immobilized plate. After the fourth panning, any clone was extracted arbitrarily from the SOBAG plate. The scFv expression was confirmed, specificity was confirmed by human MCP-1 ELISA and a nucleotide sequence was analyzed.

EXAMPLE 3

Human MCP-1 ELISA for Screening

For screening the isolated clones, ELISA was performed as follows: Human MCP-1 and human MIP-1α (macrophage inflammatory protein 1-α) were immobilized on an ELISA plate for screening. Each 2 μg/mL of a human MCP-1 or human MIP-1α, or 2.5 μg/mL of a human serum albumin (HSA) were placed in an ELISA plate (Nunc) which was kept standing at 4° C. for 16 hours for immobilization. To the immobilized plate was added 400 μL/well of a PBS solution containing 0.5% BSA, 0.5% gelatin and 5% skimmed milk and was kept standing at 4° C. for 2 hours for blocking.

To the plate was added 40 μL/well of sample solutions containing scFv display phage for reaction. The sample solutions were discarded and the plate was washed with a washing solution five times. The plate was reacted with a biotin-labeled anti-M13 monoclonal antibody (Pharmacia biotech) and then with an anti-mouse IgG antibody labeled with alkaline phosphatase (AP). After washing with a washing solution five times, the plate was added with 50 μL/well of a chromogenic substrate solution, i.e. a PBS solution containing 1 g/mL p-nitrophenyl phosphate (Wako) and 10% diethanolamine (Wako), light-shielded, and developed at room temperature to 37° C. for 5 to 10 minutes. Absorbance at 405 nm was measured using Multiplate Autoreader NJ-2001 (Inter Med). As a result, all the clones assessed were confirmed to be specific to human MCP-1 (FIG. 1).

EXAMPLE 4

Sequence Analysis of Clones

A DNA nucleotide sequence of the isolated clones was determined for scFv gene VH and VL using Dye terminator cycle sequencing FS Ready Reaction kit (Applied Biosystems) (SEQ ID NOs: 1 and 6). As a result of ELISA and sequence analysis, the isolated clones were classified into four classes.

EXAMPLE 5

Expression and Purification of Fully Human Anti-human MCP-1 scFv

Plasmid DNAs were recovered from the four scFv clones MC8, MC15, MC32 and MC59 reactive with human MCP-1 isolated in Examples 2 and 3 as described above and E. coli HB1251 was transformed with said plasmid DNAs in accordance with the conventional technique. The E. coli cells were cultured overnight on 2×YT medium containing 2% glucose and then a portion of the cells were transferred to 2×YT medium free from glucose and thereto was added IPTG at a final concentration of 1 mM for overnight culture to induce expression of scFv. After completion of culture, the cells were recovered, suspended in PBS containing 1 mM EDTA and placed on ice for 30 minutes. Then, centrifugation was performed at 8,900×g for 30 minutes. A supernatant was recovered and passed through 0.45 μm filter and the filtrate was used as a starting material for purifying scFv from a periplasmic fraction.

The thus prepared starting material for purification was purified by affinity chromatography with an anti-E tag antibody in accordance with the conventional technique. After dialysis with PBS, endotoxins were removed with an endotoxin-removing column Detoxi-gel (PIERCE) in accordance with the protocol attached thereto. After concentration with Centricon (Amicon) with a molecular weight cut-off of 10,000, filtration through 0.45 μm filter provided a purified product.

EXAMPLE 6

Binding of Purified scFv with Human MCP-1

Figure 2:
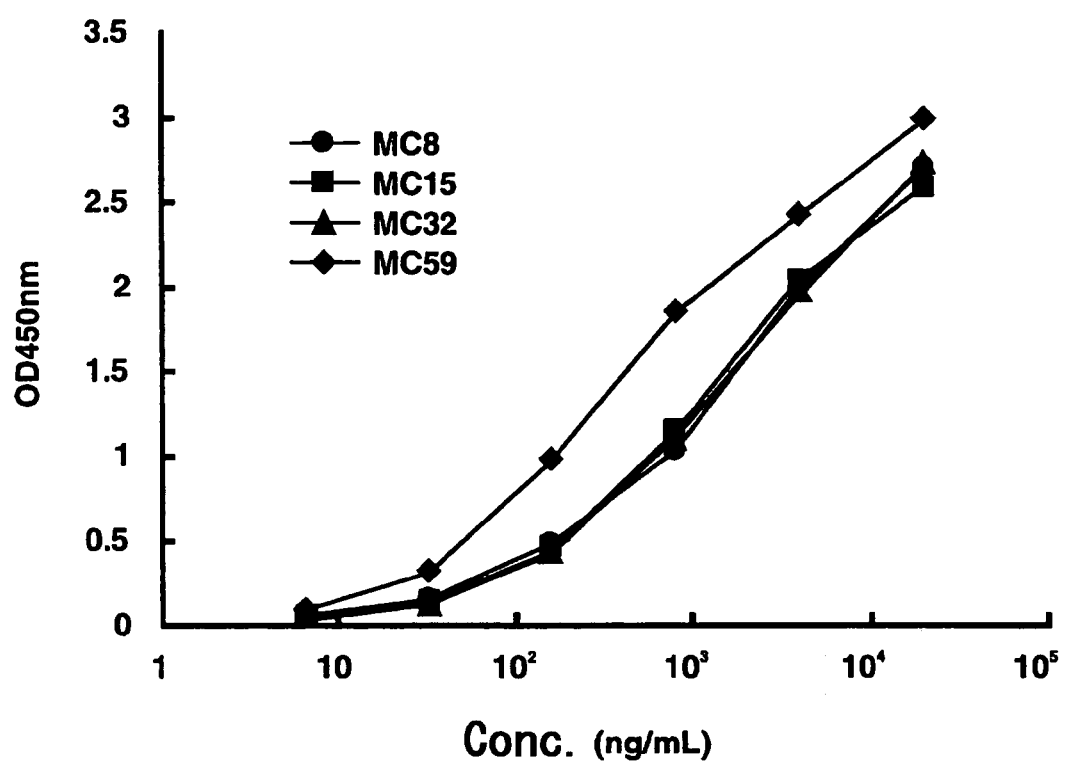
FIG. 2 is a graph showing the results of ELISA where a binding of the purified scFv derive from human with human MCP-1 was measured.

Binding of the purified scFv with human MCP-1 was then measured by ELISA. To a 96-well plate (NUNC. MAX- ISORP) immobilized with human MCP-1 prepared at 0.5 µg/mL with PBS was added 10 µL of the purified antibody for reaction at 37° C. for 1 hour. After washing five times with 0.05% Tween-PBS (hereinafter also referred to as "PBST"), the plate was further reacted with an anti-E tag antibody labeled with peroxidase at 37° C. for 1 hour. After washing five times with PBST, to the plate was added a chromogenic substrate solution for development and absorbance at 450 nm was measured to assess the binding. The results are shown in FIG. 2. All the four antibodies were found to bind to human MCP-1 in a concentration dependent manner.

EXAMPLE 7

Effect on the Cell Migration Mediated by Human MCP-1

Figure 3:
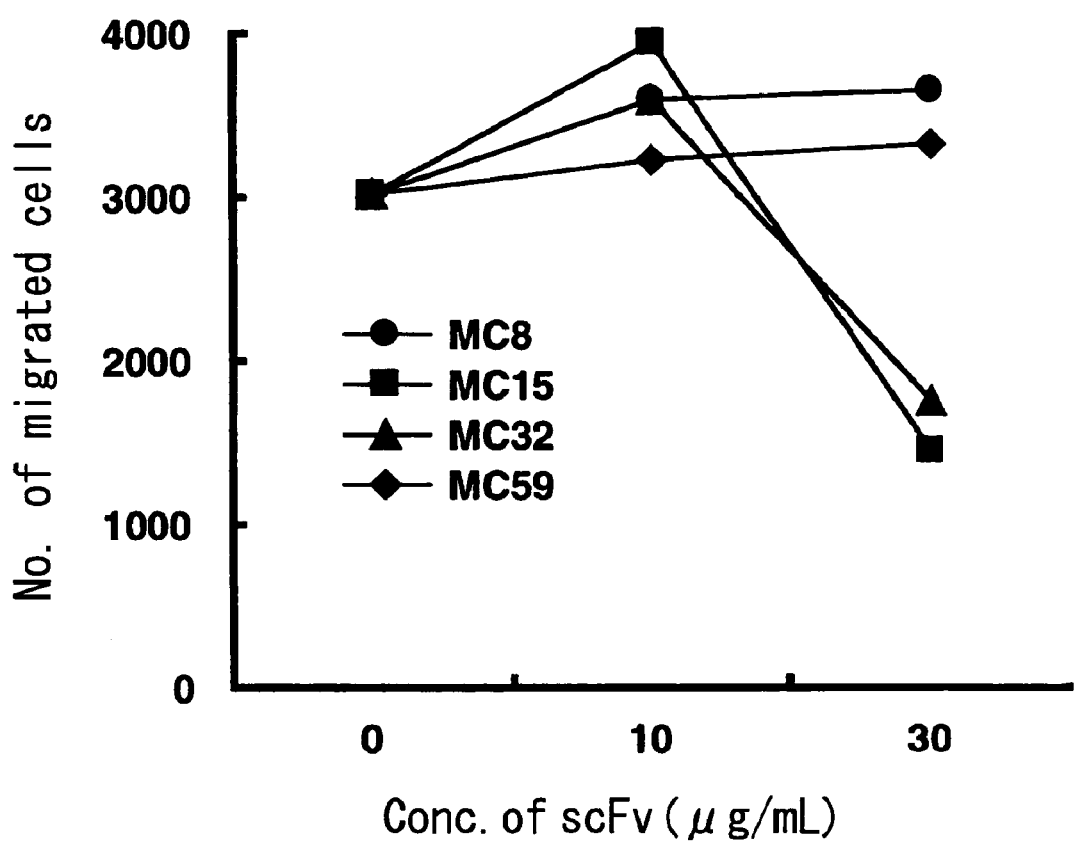
FIG. 3 is a graph showing that scFv inhibits cell migration of human monocytic cell line THP-1 mediated by human MCP-1.
Figure 4:
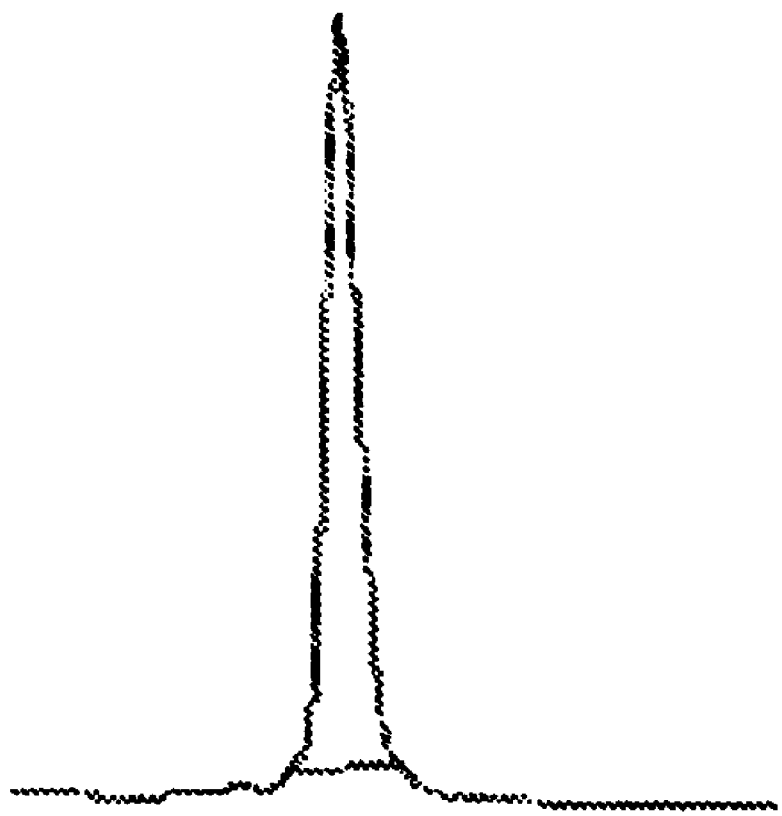
FIG. 4 shows HPLC pattern of the purified MC32 in the immunoglobulin form wherein flow rate: 0.5 mL/min.; initiation buffer: 100 mM PB, pH 7.2+0.5M NaCl.

The inhibitory activity of the antibody of the present invention to the cell migration mediated by human MCP-1 to monocytes was investigated by chemotaxis assay. Transwells with a pore size of 8 µm (Costar) were set on each well of a 24-well plate. To this 24-well plate was added 540 µL of RPMI 1640 medium containing 1% FCS (hereinafter also referred to as "1% FCS-RPMI"). Then, each equivalent amount of scFv of an adjusted concentration and $2\times10^{-8}$ M human MCP-1 (CHEMICON) were mixed and incubated at room temperature for 30 minutes. 60 µL of the reaction solution was added to a 24-well plate containing 540 µL of the medium. To Transwells were added 100 µL of 1% FCS-RPMI and $1\times10^6$ cells/mL of human monocytic cell line THP-1 (200 µL) and the plate was kept to stand at 37° C. for 4 hours. Thus, the cells reside in the upper Transwell portion that is partitioned with the 8 µm filter from the lower 24-well plate where the mixture of the antibody is placed. The cells that migrate through the filter towards the 24-well plate were counted with a Coulter counter (Coulter). The results of this assay are shown in FIG. 3. Among the four antibodies, MC15 and MC32 were found to have an inhibitory activity to the cell migration mediated by human MCP-1.

EXAMPLE 8

Construction of Plasmid Expressing Human Anti-MCP-1 Antibody in the Immunoglobulin Form From the expression plasmid in which scFv DNA of scFv clone MC32 isolated in Example 3 was incorporated, each DNA encoding VH chain and VL chain regions were amplified by PCR. Each PCR primers used for the amplification are indicated below.

```
[VH sense chain]
5'-CGT GGC TCC TGG GCC CAC AGC CAG   (SEQ ID NO: 11)
GTA CAG CTG CAG CAG TCA-3'

[VH antisense chain]
5'-TGA GGA TAC GGT GAC CGT GG-3'    (SEQ ID NO: 12)

[VL sense chain]
5'-CGT GGC TCC TGG GCC CAC AGC GAC   (SEQ ID NO: 13)
ATC CAG TTG ACC CAG TCT-3'

[VL antisense chain]
5'-ACG TTT GAT CTC CAC CTT GG-3'    (SEQ ID NO: 14)
```

The amplified DNAs of the VH chain and VL chain were each cloned into plasmid DNA pUC18, in which a leader sequence necessary for secretion in animal cells is incorporated, at the downstream of said leader sequence.

The thus obtained plasmid DNAs were digested with HindIII (TAKARA BIO INC.)-BamHI (TAKARA BIO INC.) at 37° C. for 2 hours and were electrophoresed on 2% agarose gel (TAKARA BIO INC.) to recover VH chain and VL chain DNA fragments containing the signal sequence.

The expression plasmid pCAG-H, in which the H chain constant region (hinge-CH1-CH2-CH3) gene of a human antibody IgG1 is incorporated, was digested with HindIII-BamHI at 37° C. for 2 hours. To the prepared vector DNA fragment was inserted the HindIII-BamHI fragment of the VH chain previously prepared. *E. coli* HB101 cells were transformed with the resulting expression plasmid and the plasmid was prepared from drug (ampicillin) resistant colonies and treated with the restriction enzymes to confirm the insertion of the VH chain.

Likewise, the VL chain DNA fragment was inserted into the expression plasmid pCAG-L in which the L chain (K chain) constant region (CK) gene of a human antibody is incorporated.

EXAMPLE 9

Transient Expression of Human Anti-MCP-1 Antibody MC32 in the Immunoglobulin Form in Animal Cells and Purification thereof BMT-10 cells were used for transient expression. Each 5 mL of BMT-10 cells maintained on D'MEM (Invitrogen) with 8% FCS (Invitrogen) were dispensed into sterilized small laboratory dishes (diameter 6 cm; Corning) at a cell concentration of $1.5\times10^5$ cells/mL and incubated in $CO_2$ incubator at 37° C. overnight. After washing the cells twice with PBS (SIGMA), the culture medium was replaced with 5 mL of OPTI-MEM (Invitrogen) with a lower serum level. Two disposable centrifuge tubes (FALCON) made of polystyrene were provided. In one tube, 10 µL of Lipofectamine reagent (Invitrogen) and 90 µL of OPTI-MEM culture medium were mixed together (hereinafter referred to as "Lipofectamine solution"). In the other tube, each 3 µg of the expression plasmid DNAs of the H chain and L chain as previously prepared were added and thereto 10 µL of OPTI-MEM was further added (hereinafter referred to as "DNA solution".). The DNA solution was added drop by drop to the Lipofectamine solution and the mixture was stirred at room temperature for 30 minutes for reaction. After completion of the reaction, a total amount (200 µL) of the solution was added drop by drop to laboratory dish and incubated in $CO_2$ incubator at 37° C. for 6 hours. After six hours, the culture medium was removed by suction, D'MEM with 8% FCS was gently added and the dish was incubated at 37° C. for 4 days. After four days, supernatant was recovered and passed through 0.22 µm filter and the filtrate was used as a starting material for purification.

Purification was performed in accordance with the conventional technique using a purification system of Biologic Duo Flow (BIO RAD) and Protein G column (Pharmacia). Specifically, the Protein G column was equilibrated with PBS and then 50 mL of the above culture supernatant was applied to the column at a flow rate of 1 mL/min. After washing the column with PBS at a 50-folds larger volume than a gel bed, elution was carried out with 0.1M glycine-HCl, pH2.7. Each 1 mL of the eluate was recovered to an ET free disposable tube (FALCON 2063 etc.) to which 50 µl of 1M Tris-HCl, pH9.0 was previously added for neutralization. Absorbance at 280 nm was immediately measured for each fraction with a spectrophotometer and major fractions were pooled (normally 2 mL) and were dialyzed against PBS at 4° C. overnight. Purification assay of the purified

EXAMPLE 10

Binding of Purified MC32 Antibody in the Immunoglobulin Form with MCP-1

Figure 5:
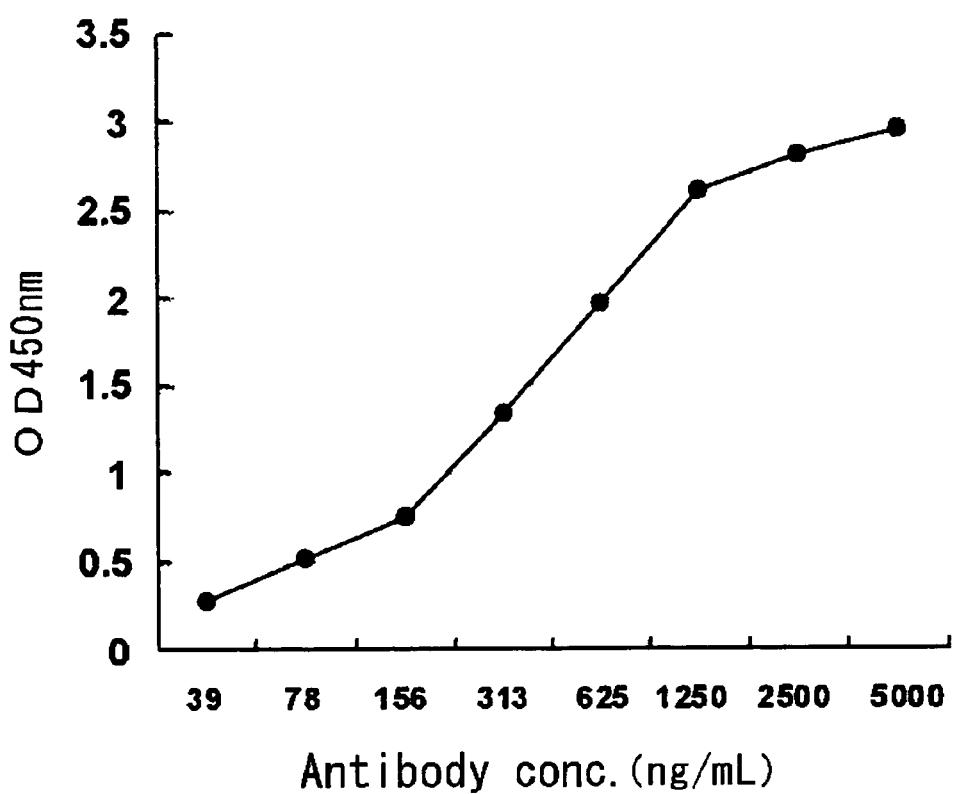
FIG. 5 is a graph showing a binding of the purified MC32 in the immunoglobulin form with MCP-1.

Binding of the purified MC32 antibody in the immunoglobulin form with MCP-1 was assessed by ELISA. After a 96-well plate (Maxisorp; Nunc) immobilized with human MCP-1 (Chemicon) prepared at 0.5 µg/mL with PBS was blocked with 1% BSA/PBS, the purified anti-MCP-1 antibody MC32 in the immunoglobulin form was used with two-fold serial dilution with 1% BSA-0.05% Tween/PBS starting from 5 µg/mL. After reaction at 37° C. for 1 hour, the plate was washed five times with 0.05% Tween/PBS and further reacted with an anti-human IgG antibody labeled with peroxidase at 37° C. for 1 hour. After washing five times with PBST, a chromogenic substrate TMBZ was added to the plate for development and absorbance at 450 nm was measured to assess the binding. The results are shown in FIG. 5. The purified MC32 antibody in the immunoglobulin form bound to MCP-1 in a concentration dependent manner as in the case of scFv.

The invention claimed is:

1. An isolated DNA molecule coding for a single chain Fv (scFv) of a human anti-human MCP-1 antibody that binds to human MCP-1, said DNA molecule comprising a DNA coding for a VH chain of said human anti-human MCP-1 antibody combined with a DNA coding for a VL chain of said human anti-human MCP-1 antibody, wherein complementarity determining regions (CDR1 to CDR3) of said VH chain have the following amino acid sequences:

```
CRD1:  Ser Tyr Ala Ile Ser,            (SEQ ID NO: 3)

CDR2:  Gly Phe Asp Pro Glu Asp Gly     (SEQ ID NO: 4)
       Glu Thr Ile Tyr Ala Gln Lys
       Phe Gln Gly
       and CDR3:  Asp Leu Gly Gly Gly Asp Tyr     (SEQ ID NO: 5)
       Tyr Tyr Gly Met Asp Val
``` and complementarity determining regions (CDR1 to CDR3) of said VL chain have the following amino acid sequences:

```
CDR1:  Arg Ser Ser Gln Ser Ile Asn     (SEQ ID NO: 8)
       Thr Tyr Leu His,

CDR2:  Ala Ala Ser Thr Leu Gln Ser     (SEQ ID NO: 9)
       and

CDR3:  Gln Gln Ser Phe Thr Thr Pro     (SEQ ID NO: 10)
       Leu Thr.
```

2. An isolated DNA molecule coding for a single chain Fv (scFv) of a human anti-human MCP-1 antibody that binds to human MCP-1, said DNA molecule comprising a DNA coding for a VH chain of said human anti-human MCP-1 antibody combined with a DNA coding for a VL chain of said human anti-human MCP-1 antibody, wherein said VH chain has the amino acid sequence depicted in SEQ ID NO: 2 and said VL chain has the amino acid sequence depicted in SEQ ID NO: 7.

3. The isolated DNA molecule of claim 2, wherein said VH chain consists of the amino acid sequence depicted in SEQ ID NO: 2 and said VL chain consists of the amino acid sequence depicted in SEQ ID NO: 7.

4. An isolated DNA molecule coding for a human anti-human MCP-1 antibody that binds to human MCP-1, said DNA molecule comprising a DNA coding for a VH chain of said human anti-human MCP-1 antibody combined with a DNA coding for a human antibody CH chain and a DNA coding for a VL chain of said human anti-human MCP-1 antibody combined with a DNA coding for a human antibody CL chain, wherein complementarity determining regions (CDR1 to CDR3) of said VH chain have the following amino acid sequences:

```
CRD1:  Ser Tyr Ala Ile Ser,            (SEQ ID NO: 3)

CDR2:  Gly Phe Asp Pro Glu Asp Gly     (SEQ ID NO: 4)
       Glu Thr Ile Tyr Ala Gln Lys
       Phe Gln Gly
       and CDR3:  Asp Leu Gly Gly Gly Asp Tyr     (SEQ ID NO: 5)
       Tyr Tyr Gly Met Asp Val
``` and complementarity determining regions (CDR1 to CDR3) of said VL chain have the following amino acid sequences:

```
CRD1:  Arg Ser Ser Gln Ser Ile Asn    (SEQ ID NO: 8)
       Thr Tyr Leu His,

CDR2:  Ala Ala Ser Thr Leu Gln Ser    (SEQ ID NO: 9)
       and

CDR3:  Gln Gln Ser Phe Thr Thr Pro    (SEQ ID NO: 10)
       Leu Thr.
```

5. An isolated DNA molecule coding for a human anti-human MCP-1 antibody that binds to human MCP-1, said DNA molecule consisting of a DNA coding for a VH chain of said human anti-human MCP-1 antibody combined with a DNA coding for a human antibody CH chain and a DNA coding for a VL chain of said human anti-human MCP-1 antibody combined with a DNA coding for a human antibody CL chain, wherein said VH chain has the amino acid sequence depicted in SEQ ID NO: 2 and said VL chain has the amino acid sequence depicted in SEQ ID NO: 7.

6. An isolated DNA molecule coding for a human anti-human MCP-1 antibody fragment that binds to human MCP-1, said DNA molecule consisting of a DNA coding for the VH chain of said human anti-human MCP-1 antibody combined with a DNA coding for a portion of a human antibody CH chain and a DNA coding for a VL chain of said human anti-human MCP-1 antibody combined with a DNA coding for a portion of a human antibody CL chain, wherein complementarity determining regions (CDR1 to CDR3) of said VH chain have the following amino acid sequences:

```
CRD1:  Ser Tyr Ala Ile Ser,            (SEQ ID NO: 3)

CDR2:  Gly Phe Asp Pro Glu Asp Gly     (SEQ ID NO: 4)
       Glu Thr Ile Tyr Ala Gln Lys
       Phe Gln Gly
       and CDR3:  Asp Leu Gly Gly Gly Asp Tyr     (SEQ ID NO: 5)
       Tyr Tyr Gly Met Asp Val
``` and complementarity determining regions (CDR1 to CDR3) of said VL chain have the following amino acid sequences:
CDR1: Arg Ser Ser Gln Ser Ile Asn Thr Tyr Leu His (SEQ ID NO: 8),
CDR2: Ala Ala Ser Thr Leu Gln Ser (SEQ ID NO: 9) and
CDR3: Gln Gln Ser Phe Thr Thr Pro Leu Thr (SEQ ID NO: 10).

7. An isolated DNA molecule coding for a human anti-human MCP-1 antibody fragment that binds to human MCP-1, said DNA molecule consisting of a DNA coding for the VH chain of said human anti-human MCP-1 antibody combined with a DNA coding for a portion of a human antibody CH chain and a DNA coding for a VL chain of said human anti-human MCP-1 antibody combined with a DNA coding for a portion of a human antibody CL chain, wherein said VH chain has the amino acid sequence depicted in SEQ ID NO: 2 and said VL chain has the amino acid sequence depicted in SEQ ID NO: 7.

8. An isolated DNA molecule coding for a human anti-human MCP-1 antibody fragment that binds to human MCP-1, said DNA molecule consisting of the scFv coding DNA molecule of claim 1 combined with either a DNA coding for a portion of a human antibody CH chain or with a DNA coding for a portion of a human antibody CL chain, wherein complementarity determining regions (CDR1 to CDR3) of said VH chain have the following amino acid sequences;

```
CRD1:  Ser Tyr Ala Ile Ser,            (SEQ ID NO: 3)

CDR2:  Gly Phe Asp Pro Glu Asp Gly     (SEQ ID NO: 4)
       Glu Thr Ile Tyr Ala Gln Lys
       Phe Gln Gly
       and CDR3:  Asp Leu Gly Gly Gly Asp Tyr     (SEQ ID NO: 5)
       Tyr Tyr Gly Met Asp Val
``` and complementarity determining regions (CDR1 to CDR3) of said VL chain have the following amino acid sequences:
CDR1: Arg Ser Ser Gln Ser Ile Asn Thr Tyr Leu His (SEQ ID NO: 8),
CDR2: Ala Ala Ser Thr Leu Gln Ser (SEQ ID NO: 9) and
CDR3: Gln Gln Ser Phe Thr Thr Pro Leu Thr (SEQ ID NO: 10).

9. The isolated DNA molecule coding for a human anti-human MCP-1 antibody fragment that binds to human MCP-1, said DNA molecule consisting of the scFv coding DNA molecule of claim 1 combined with either a DNA coding for a portion of a human antibody CH chain or with a DNA coding for a portion of a human antibody CL chain, wherein said VH chain has an amino acid sequence depicted in SEQ ID NO: 2 and said VL chain has the amino acid sequence depicted in SEQ ID NO: 7.

10. The isolated DNA molecule of claim 1 which consists of said DNA coding for a VH chain of said human anti-human MCP-1 antibody combined with said DNA coding for a VL chain of said human anti-human MCP-1 antibody.

* * * * *